(12) United States Patent
Gregg et al.

(10) Patent No.: US 9,727,919 B2
(45) Date of Patent: Aug. 8, 2017

(54) SYSTEMS AND METHODS FOR REDUCING MEDICAL CLAIMS FRAUD

(75) Inventors: Robert S. Gregg, Portland, OR (US); Christopher Allen Kane, North Plains, OR (US); Christine Clementina Arevalo, Beaverton, OR (US)

(73) Assignee: Identity Theft Guard Solutions, Inc., Portland, OR (US)

( * ) Notice: Subject to any disclaimer, the term of this patent is extended or adjusted under 35 U.S.C. 154(b) by 0 days.

(21) Appl. No.: 13/296,159

(22) Filed: Nov. 14, 2011

(65) Prior Publication Data
US 2013/0124223 A1   May 16, 2013

(51) Int. Cl.
*G06Q 40/08*   (2012.01)
*G06Q 50/24*   (2012.01)
*G06Q 30/00*   (2012.01)
*G06Q 10/10*   (2012.01)

(52) U.S. Cl.
CPC ............ *G06Q 40/08* (2013.01); *G06Q 10/10* (2013.01); *G06Q 30/0185* (2013.01); *G06Q 50/24* (2013.01)

(58) Field of Classification Search
CPC ...... G06Q 50/22; G06Q 20/401; G06Q 30/04; G06F 19/328
USPC ............................................................ 726/7
See application file for complete search history.

(56) References Cited

U.S. PATENT DOCUMENTS

| | | | |
|---|---|---|---|
| 6,985,922 B1 | 1/2006 | Bashen et al. | |
| 7,739,132 B2 * | 6/2010 | Denny et al. | 705/4 |
| 7,813,944 B1 * | 10/2010 | Luk et al. | 705/4 |
| 7,996,374 B1 | 8/2011 | Jones et al. | |
| 8,185,931 B1 | 5/2012 | Reeves | |
| 8,332,959 B2 | 12/2012 | Chen et al. | |
| 8,707,445 B2 | 4/2014 | Sher-Jan et al. | |
| 8,763,133 B2 | 6/2014 | Sher-Jan et al. | |
| 2002/0029157 A1 * | 3/2002 | Marchosky | 705/3 |
| 2002/0091549 A1 * | 7/2002 | Provost | G06Q 40/00 705/4 |
| 2002/0120477 A1 | 8/2002 | Jinnett | |
| 2003/0135397 A1 * | 7/2003 | Halow et al. | 705/4 |
| 2003/0225690 A1 * | 12/2003 | Eaton | 705/40 |
| 2004/0098285 A1 | 5/2004 | Breslin et al. | |

(Continued)

FOREIGN PATENT DOCUMENTS

WO   WO 2012027694 A2 *   3/2012   ........... G06Q 20/102

OTHER PUBLICATIONS

Ortega, Pedro, "Medical Claim Fraud/Abuse Detection System based on Data Mining: A Case Study in Chile," Conference on Data Mining 2006.*

(Continued)

*Primary Examiner* — Elaine Gort
*Assistant Examiner* — John Go
(74) *Attorney, Agent, or Firm* — Carr & Ferrell LLP

(57) ABSTRACT

Various embodiments of the present disclosure may be comprised of systems and methods for reducing fraudulent use of a medical identity to obtain medical goods or services. Identification information may be received for a medical insurance account of a medical consumer. Medical claims data associated with the medical insurance account may be received, and the medical claims data may be transmitted to the medical consumer. A confirmation status may be received from the medical consumer for the medical claims data.

17 Claims, 7 Drawing Sheets

(56) References Cited

U.S. PATENT DOCUMENTS

| | | | |
|---|---|---|---|
| 2004/0193907 A1 | 9/2004 | Patanella | |
| 2005/0044357 A1* | 2/2005 | Fano | G06Q 10/10 713/164 |
| 2005/0273360 A1* | 12/2005 | Drucker | G06Q 30/04 705/2 |
| 2006/0020495 A1* | 1/2006 | Baker et al. | 705/4 |
| 2006/0101508 A1* | 5/2006 | Taylor | G06F 21/32 726/7 |
| 2006/0247947 A1* | 11/2006 | Suringa | 705/2 |
| 2006/0277071 A1* | 12/2006 | Shufeldt | 705/3 |
| 2007/0038484 A1* | 2/2007 | Hoffner | G06Q 40/08 705/4 |
| 2007/0078668 A1* | 4/2007 | Pathria | G06F 21/31 726/7 |
| 2007/0136814 A1 | 6/2007 | Lee et al. | |
| 2008/0059230 A1* | 3/2008 | Manning et al. | 705/2 |
| 2008/0162496 A1* | 7/2008 | Postrel | 707/10 |
| 2008/0177760 A1* | 7/2008 | Fein | 707/100 |
| 2009/0070434 A1* | 3/2009 | Himmelstein | 709/217 |
| 2009/0210256 A1* | 8/2009 | Upadhyayula et al. | 705/4 |
| 2009/0313049 A1* | 12/2009 | Joao et al. | 705/3 |
| 2010/0042440 A1* | 2/2010 | Joao | G06F 19/322 705/3 |
| 2010/0114607 A1* | 5/2010 | Kress et al. | 705/3 |
| 2010/0199338 A1* | 8/2010 | Craddock et al. | 726/7 |
| 2010/0262668 A1* | 10/2010 | Piett et al. | 709/206 |
| 2012/0331567 A1 | 12/2012 | Shelton | |
| 2013/0212692 A1 | 8/2013 | Sher-Jan et al. | |
| 2014/0304822 A1 | 10/2014 | Sher-Jan et al. | |
| 2015/0113663 A1 | 4/2015 | Sher-Jan et al. | |
| 2016/0021133 A1 | 1/2016 | Sher-Jan et al. | |

OTHER PUBLICATIONS

Non-Final Office Action, Apr. 9, 2013, U.S. Appl. No. 13/396,558, filed Feb. 14, 2012.

Notice of Allowance, Dec. 23, 2013, U.S. Appl. No. 13/396,558, filed Feb. 14, 2013.

Non-Final Office Action, Mar. 14, 2013, U.S. Appl. No. 13/691,661, filed Nov. 30, 2012.

Non-Final Office Action, Oct. 1, 2013, U.S. Appl. No. 13/691,661, filed Nov. 30, 2012.

Notice of Allowance, Feb. 10, 2014, U.S. Appl. No. 13/691,661, filed Nov. 30, 2012.

Non-Final Office Action, Mar. 4, 2015, U.S. Appl. No. 14/311,253, filed Jun. 21, 2014.

Non-Final Office Action, Nov. 13, 2015, U.S. Appl. No. 14/588,159, filed Dec. 31, 2014.

* cited by examiner

500

505

510

Please indicate which of the following
medical goods or services are accurate:

Yes  No

1. Dr. Wilson, San Jose, CA, February 10, 2011.   ☐  ☐
   Annual physical.

2. Northside Medical Supply, San Francisco, CA,   ☐  ☐
   March 7, 2011. Purchased walking cane.

3. Mountain Top Physical Therapy, Milpitas, CA,   ☐  ☐
   June 23, 2011. Rehabilitate left knee.

4. Bob's Pharmacy, Cupertino, CA, June 27, 2011.  ☐  ☐
   Fill prescription for 1-month supply of
   Naproxen.

ENTER

SYSTEMS AND METHODS FOR REDUCING MEDICAL CLAIMS FRAUD

FIELD OF THE INVENTION

The present disclosure relates generally to fraud prevention, and more specifically to reducing fraudulent use of medical identities.

BACKGROUND

Medical identity theft is becoming increasingly prevalent in the U.S. Privacy experts have stated that it is the fastest growing identity related crime faced by American consumers. In the U.S. alone, medical identity theft is estimated to represent 10 percent of all identity theft, affecting over 1.5 million individuals each year. Not only is medical identity crime growing, it is important to recognize that for consumers medical identity theft may be significantly worse that financial identity theft. Losses due to financial identity theft are often limited by banks and credit card companies motivated to maintain trust in banking and credit systems. With medical identity theft, personal health records can be altered, potentially exposing an individual to dangerous medical treatment. In addition, medical privacy laws may hinder correcting inaccuracies in medical records caused by medical identity theft. Despite the growth and scope of this problem, there are no effective mechanisms for individuals to monitor their medical identity, as has been done with financial identity, with the intent of detecting medical identity theft and healthcare provider fraud.

SUMMARY

Various embodiments of the present disclosure may be comprised of systems and methods for reducing fraudulent use of a medical identity to obtain medical goods or services. Identification information may be received for a medical insurance account of a medical consumer. Medical claims data associated with the medical insurance account may be received, and the medical claims data may be transmitted to the medical consumer. A confirmation status may be received from the medical consumer for the medical claims data. In various embodiments, the confirmation status may comprise a confirmation of the accuracy of the medical claims data.

BRIEF DESCRIPTION OF THE DRAWINGS

FIG. 5 is a screen shot showing an input screen for confirming medical claims data according to various embodiments.

DETAILED DESCRIPTION

Figure 1:
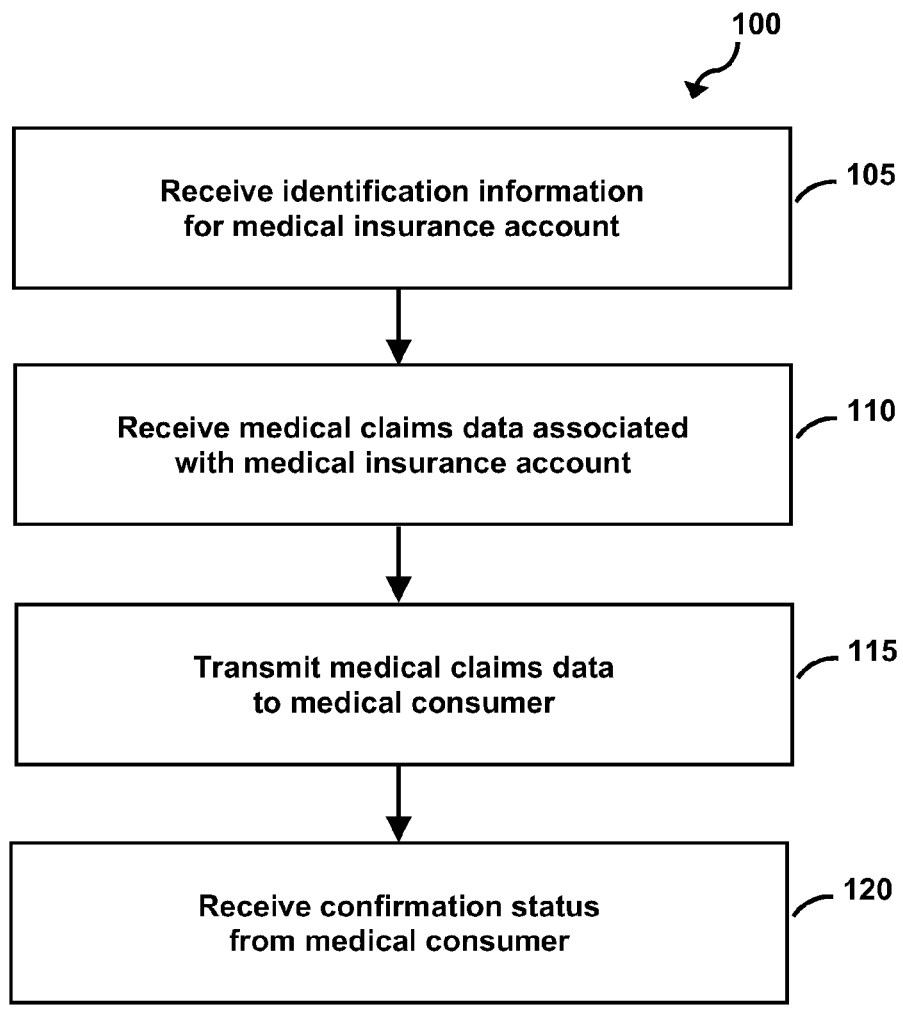
FIG. 1 is an exemplary flow diagram of a method for reducing fraudulent use of a medical identity to obtain medical goods or services according to various embodiments.

Various embodiments of the present disclosure include systems and methods for reducing fraudulent use of a medical identity to obtain medical goods or services. Identification information may be received for a medical insurance account of a medical consumer. Medical claims data associated with the medical insurance account may be received, and the medical claims data may be transmitted to the medical consumer. A confirmation status may be received from the medical consumer for the medical claims data. In various embodiments, the confirmation status may comprise a confirmation that the medical claims are accurate, a confirmation that the medical claims data are inaccurate, or a notification that the medical consumer is unable to determine the accuracy of the medical claims data. In some embodiments, no confirmation status may be received from the medical consumer.

The systems and methods of the present disclosure may be applied to medical claims data to provide an indication of whether some portion of the medical claims data may be fraudulent due to misappropriation, or theft, of a medical identity. Misappropriation of a medical identity may occur in a variety of situations. One common situation is when a medical identity of a medical consumer is fraudulently obtained by another person, and that other person uses the medical identity to obtain medical goods or services. A second common situation is when a real or fictitious provider of medical goods or services bills a provider of medical insurance for medical goods or services that were not rendered, using a fraudulently obtained medical identity of the medical consumer. Yet another situation may involve legitimately obtained medical identities. For example, a medical clinic may provide legitimate medical services to patients, but uses the medical identities obtained from those patients to fraudulently bill the medical insurance provider for additional medical goods or services that the patients did not receive. In each of these situations, the medical consumer may not be aware that the medical identity has been misappropriated, nor that medical goods or services have been billed in the name of the medical identity. In other situations, the medical consumer may know that the other person has obtained the medical identity, such as when the medical consumer provides his or her medical insurance identification card to the other person so that the other person may obtain medical goods or services.

In various embodiments, medical goods or services involve some type of direct interaction between the medical consumer and a provider of medical goods or services. The provider of the medical goods or services may be any person in the medical community including, but limited to, doctors, dentists, psychologists, therapists, chiropractors, nurses, assistants, hygienists, technicians, trainers, nutritionists, emergency medical technicians, social workers, and like health practitioners and professionals; prescription medications; laboratory services; high technology diagnostic services, tests, and procedures; transportation by ambulance; blood and blood products; durable medical equipment and associated supplies; eyeglasses and corrective lenses; external prosthetic, orthotic and corrective devices; internal medical devices; and the like.

FIG. 1 is a flow chart of various embodiments of a method 100 for reducing fraudulent use of a medical identity to obtain medical goods or services. The method 100 may be carried out by a provider of a service to reduce or prevent fraudulent use of medical identities. At step 105, identification information for a medical insurance account of a medical consumer may be received. The identification information may be provided by the medical consumer when, for example, the medical consumer signs up for a service offered by the fraud prevention service provider to reduce or prevent fraudulent use of the medical identity of the medical consumer. The medical consumer may provide the identification information online by accessing a web site over the Internet, by sending an email, through a social media web site, on paper by completing one or more forms and then transmitting the forms to a provider of the service, over the phone, or any other transmittal method known in the art now or in the future. In various embodiments, the identification information may be provided by a provider of medical insurance.

The identification information provided by the medical consumer may comprise any information that may be used to link the medical consumer with the medical insurance account of the medical consumer. In various embodiments, the medical identity may comprise any information shared between the medical consumer and the medical insurance provider that is providing medical insurance coverage to the medical consumer. The identification information may comprise general information about the medical consumer, such as name, home address, home telephone and cellular telephone number, electronic mail address, social media address, social security number, name and address of an employer of the medical consumer, and the like.

The identification information may also comprise information specific to an insurance policy provided by the medical insurance provider to the medical consumer. The insurance policy information may comprise a name and address of the medical insurance provider, a policy number, a group number, a member number, a date that coverage under the insurance policy began, level of coverage, and the like.

At step 110, medical claims data associated with the medical insurance account is received by, for example, the fraud prevention service provider. In various embodiments, the medical claims data may be received from the medical insurance provider. In certain other embodiments, the medical claims data may be received from a provider of the medical goods or services.

The medical claims data may comprise any information or data that identifies particular medical goods or services reported against the medical insurance account of the medical consumer. For example, the medical claims data may comprise a name and address of the provider of the medical goods or services, such as the name of a doctor and the location of the office in which a medical service was provided. The medical claims data may also comprise a description of the goods or services provided. The description may comprise an alphanumeric medical billing code, such as Current Procedural Terminology (CPT) codes developed by the American Medical Association, or Healthcare Common Procedure Coding System (HCPCS) codes developed for Medicare use. The description may also comprise a diagnostic or procedural code, such as an International Statistical Classification of Diseases (ICD) codes. ICD codes may, for example, comprise a ICD-9-CM diagnostic code, a ICD-10-CM diagnostic code, or any other medical billing, diagnostic, or procedural code.

The description of the medical goods or services may also comprise a written description of the goods or service, such as a flu shot, a physical, a surgical procedure, a wheelchair, a prosthetic limb, a glucose test meter, a prescription medication, and the like. The written description may comprise a description of the medical billing, diagnostic or procedural code. Additionally, the medical claims data may comprise the date or dates that the medical goods or services were provided.

The medical claims data may then be transmitted to the medical consumer (step 115). The transmittal may occur via an email message, a message transmitted via a social media web site, a telephone call, a letter, or any other transmittal method known in the art now or in the future. The transmittal may be in a secure mode to protect the privacy interests of the medical consumer. For example, the transmittal may be encoded such that a password may have to be entered prior to viewing. In various embodiments, the transmittal may be a notice that medical claims data have been received. In this situation, the medical consumer may securely log into a web site (or make contact through another mechanism, such as a telephone call) and view the medical claims data.

At step 120, a confirmation status may be received from the medical consumer regarding the medical claims data. The medical consumer may provide a variety of responses to the medical claims data. The medical consumer may confirm that the medical claims data are accurate. For example, the medical claims data may specify that a claim was made against the medical insurance account of the medical consumer for a visit to a certain doctor on a given date. If the medical consumer recognizes the visit as one that the medical consumer actually made, then the medical consumer may provide a confirmation that the medical claims data are accurate.

However, the medical consumer may not recognize the medical goods or services specified in the medical claims data. In this situation, the medical consumer may be reasonably certain that he or she did not receive the medical goods or services. For example, the medical consumer may be certain that he or she was out of town on the date specified and could not have received the medical goods or services on the date or at the location specified. Thus, the medical consumer may provide confirmation that the medical claims data are inaccurate.

The medical consumer also may not recognize the medical goods or services because the medical consumer cannot recall whether the medical claims data are accurate, particularly if a date specified in the medical claims data is not recent. For example, the medical claims data may indicate that the medical consumer visited a certain doctor six months ago. The medical consumer may recognize the doctor as being one that he or she has visited, but is unsure whether the date of the visit is correct. Here, the medical consumer may provide a notification that he or she is unable to determine the accuracy of the medical claims data.

In various embodiments, the confirmation status may comprise a notification that the medical consumer has viewed the medical claims data. For example, when the medical consumer opens an email message containing the medical claims data, a notification may be automatically sent that the email message was viewed. In other embodiments, the medical consumer may log onto a website to view the medical claims data. In this situation, a notification may be sent that the medical consumer accessed the website containing the medical claims data.

A variety of actions may then be taken based on the confirmation status received from the medical consumer. If the confirmation status indicates that the medical claims data are accurate, then no further action may be taken. In various embodiments, a notification may be sent to the medical insurance provider that the medical consumer confirmed the medical claims data as accurate. The medical insurance provider may then take appropriate action with the claim. In the situation where the medical consumer indicates that the medical claims data are inaccurate, then the medical claims data may be flagged as being potentially fraudulent. Further investigation into the claim may be warranted, and the medical insurance provider may be notified of this status.

When the medical consumer is unable to determine the accuracy of the medical claims data, this may or may not indicate a possible fraudulent claim. Therefore, the claim may be flagged as needing further investigation, and the medical insurance provider may be so notified. In various embodiments, further communications may be initiated with the medical consumer when the medical consumer either confirms that the medical claims data are inaccurate, or is unable to determine the accuracy of the medical claims data.

Another possible situation is that the medical consumer does not respond to the transmittal of the medical claims data. In various embodiments, the claim may be assumed to be accurate and the medical consumer neglected to respond as such. Alternatively, the medical claims data may be flagged for further investigation, and notice provided to the medical insurance provider. In various embodiments, a reminder may be transmitted to the medical consumer if no response is received after a predetermined period of time. The reminder may be transmitted by the fraud prevention service provider, or by another entity tasked with this responsibility.

Figure 2:
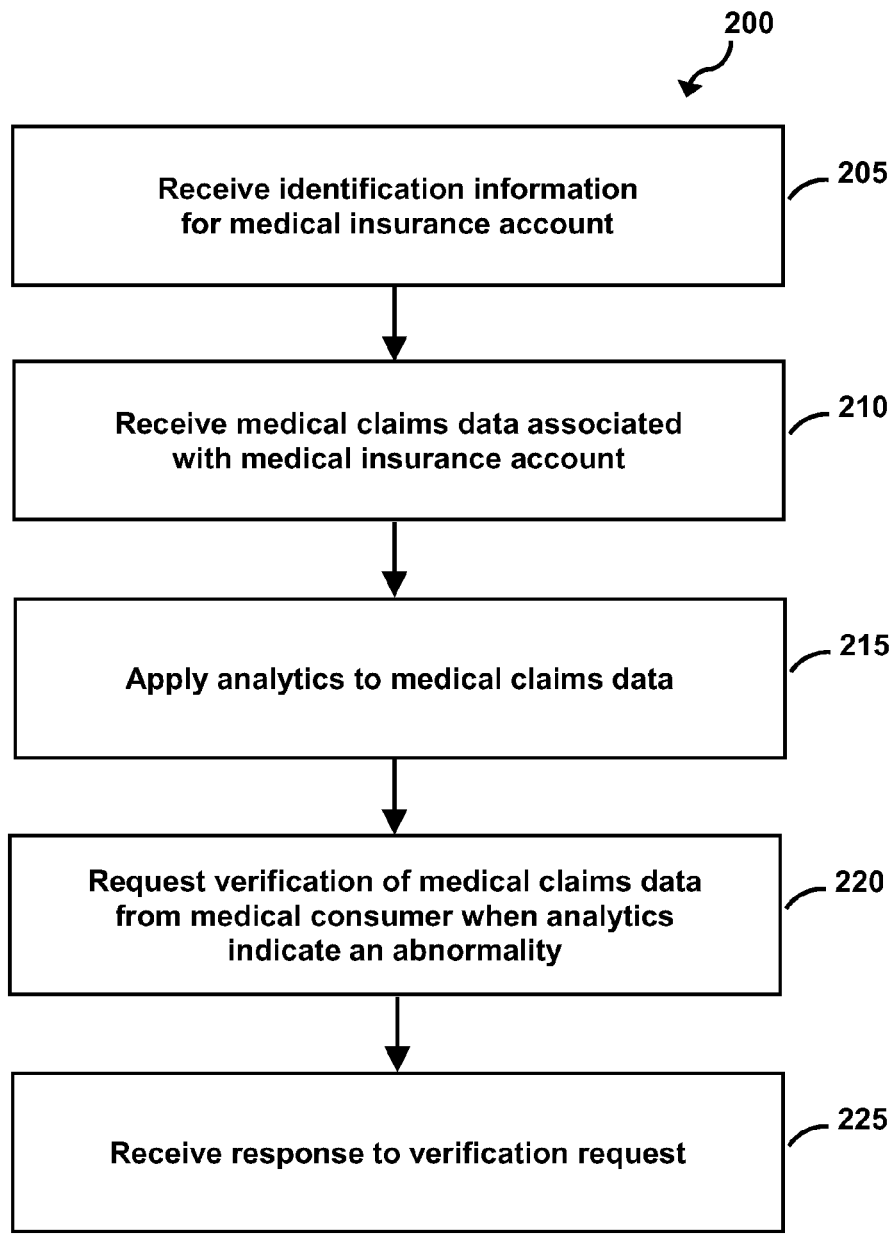
FIG. 2 is an exemplary flow diagram of a method for reducing fraudulent use of a medical identity to obtain medical goods or services according to various embodiments.

FIG. 2 is a flow chart of various embodiments of a method 200 for reducing fraudulent use of a medical identity to obtain medical goods or services, wherein analytics may be applied to the medical claims data. Identification information for a medical insurance account of a medical consumer may be received (step 205) and medical claims data associated with the medical insurance account received (step 210) as described previously for steps 105 and 110, respectively of method 100. At step 215, analytics may be applied to the medical claims data. The analytics may comprise one or more evaluations of the medical claims data to determine whether the medical claims data may be fraudulent. If the analytics indicate an abnormality with the medical claims data, a request may be made to the medical consumer for a verification of the medical claims data (step 220). A response from the medical consumer to the verification request may then be received (step 225).

Various embodiments of method 200 may serve to filter a portion of the medical claims data as having a high probability of being legitimate. These medical claims may not be transmitted to the medical consumer, thereby limiting the volume of communications to and from the medical consumer to only those medical claims that have a higher probability of being fraudulent. Various embodiments of method 200 may be desirable when the medical consumer has a higher number of medical claims than a prescribed norm. For example, the medical consumer may have a chronic illness that requires repeated visits to certain healthcare providers. After verifying many legitimate medical claims, the medical consumer may not see the value in continuing to provide verifications and fail to respond to further requests for verification. By filtering the medical claims data with analytics, the medical consumer may receive fewer requests for verification and may be more likely to be responsive to the requests. Various embodiments may also apply the analytics to filter a portion of the medical claims data as having a high probability of being fraudulent, as discussed below.

Figure 3:
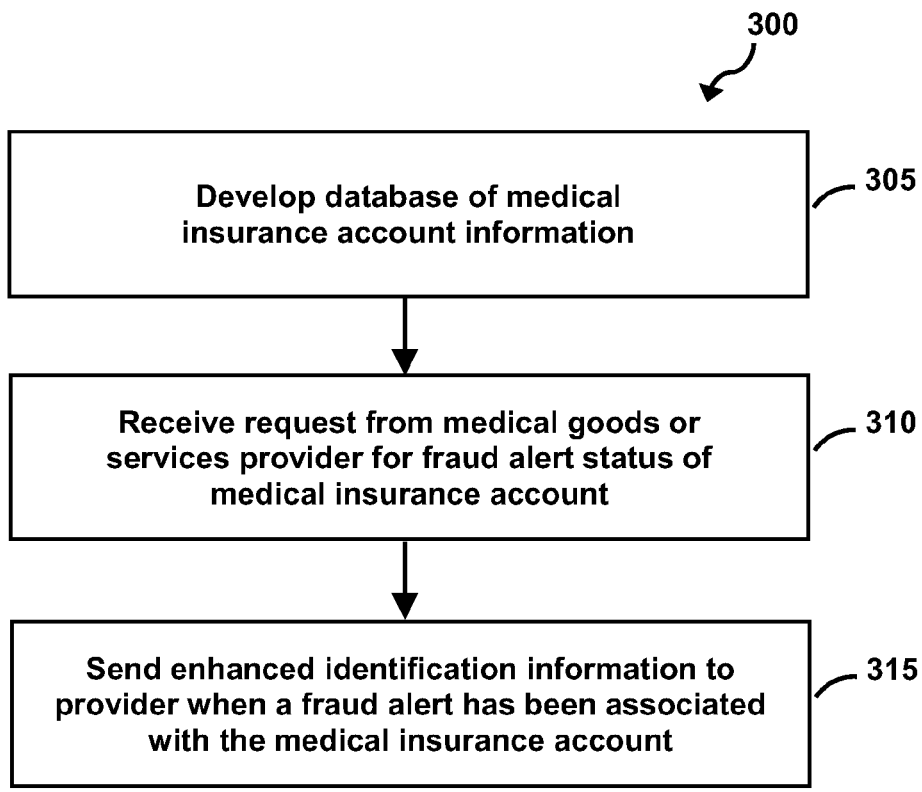
FIG. 3 is an exemplary flow diagram of a method for reducing fraudulent use of a medical identity to obtain medical goods or services according to various embodiments.

Various embodiments may be used to reduce fraudulent use of a medical identity to obtain medical goods or services by identifying the fraudulent use at the point of providing the medical goods or services, as illustrated by method 300 in FIG. 3. At step 305, a database is developed of medical insurance account information for a plurality of medical consumers. The database may contain any of the identification information described previously to identify the medical consumer and the medical insurance account. In various embodiments, pre-approval may be obtained from the medical consumer to utilize the medical insurance account information for identification purposes. Within the database, a fraud alert status may be associated with each medical insurance account. The fraud alert status may comprise a "yes" or "no" status, wherein a status of "yes" may indicate that some type of fraudulent or potentially fraudulent activity has been identified in relation to the medical insurance account, and a status of "no" may indicate that no fraudulent or potentially fraudulent activity has been identified in relation to the medical account. For example, in method 100, receiving a confirmation status from the medical consumer that the medical claims data may be inaccurate may set the fraud alert status to "yes." At step 310, a request may be received from a provider of medical goods or services for the fraud alert status of one of the medical insurance accounts in the database. For example, a patient may check in at a doctor's office for a scheduled visit. If the healthcare providers in the office do not recognize the patient, they may log onto a web site of a provider of a service to reduce or prevent fraudulent use of medical identities. The healthcare provider may enter identification information for the medical insurance account provided by the patient into the web site and receive the fraud alert status.

At step 315, enhanced medical consumer identification information may be sent to the provider of the medical goods or services when a fraud alert has been associated with the medical insurance account. In the above example, the enhanced medical consumer identification information may appear on the web site (e.g., on a computer monitor utilized by the healthcare provider).

The enhanced medical consumer identification information may comprise additional information to assist the healthcare provider in making a positive identification that the patient is the rightful owner of the medical identity. In various embodiments, the enhanced medical consumer identification information may comprise biometric data, such as a photographic image of the medical consumer. The enhanced medical consumer identification information may comprise unique identifying information associated with the medical consumer, such as age, height, weight, hair color, eye color, and the like.

Figure 4:
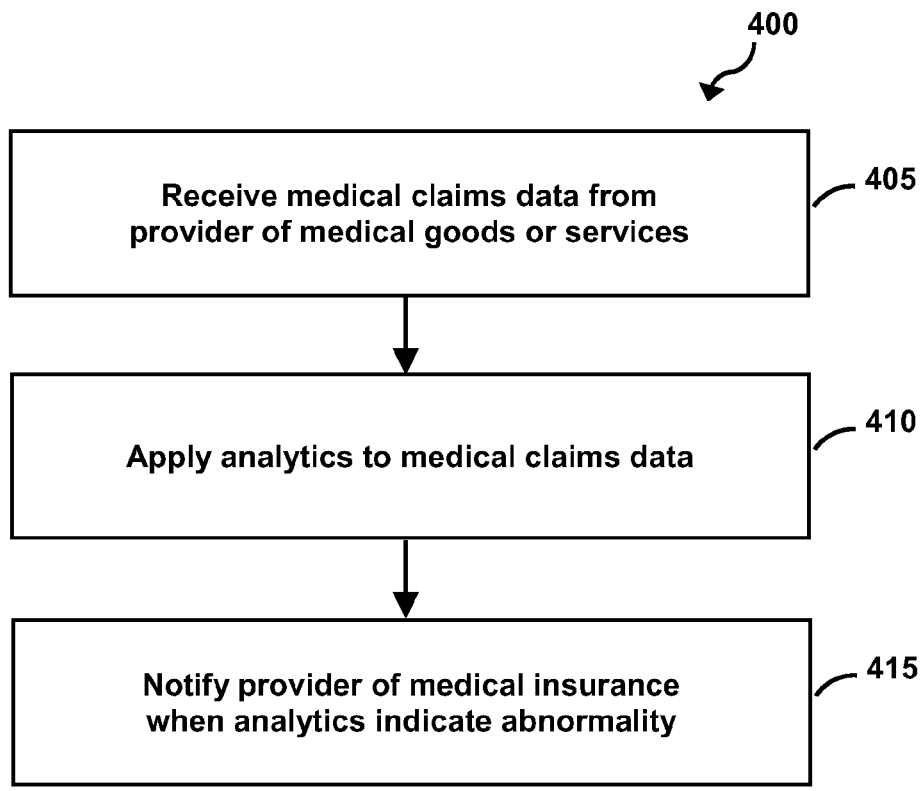
FIG. 4 is an exemplary flow diagram of a method for reducing fraudulent use of a medical identity to obtain medical goods or services according to various embodiments.

Various embodiments may be used to detect potentially fraudulent activity at a provider of medical goods or services as illustrated by method 400 in FIG. 4. At step 405, medical claims data may be received that are associated with a provider of medical goods or services. In various embodiments, the medical claims data may be provided directly by the medical goods or services provider. In alternative embodiments, the medical claims data may be provided by a medical insurance provider. Analytics may be applied to the medical claims data (step 410). As described above for method 200, the analytics may comprise one or more evaluations of the medical claims data to determine whether the medical claims data may be fraudulent. For example, a fraudulent user of a medical identity may visit several doctors to obtain multiple prescriptions for a medication. The individual doctors may not be aware that the person is acting fraudulently. However, the analytics may indicate that the person is receiving medical care from multiple doctors for the same condition. Once such an abnormality is indicated in the medical claims data, the medical insurance provider may be notified (step 415).

Various embodiments of method 400 may also be used to detect possible fraudulent actions by a provider of medical goods or services. For example, a doctor may be fraudulently diagnosing patients with a condition that requires a costly treatment or medical device. The treatment (e.g., a prescription drug) or medical device may then be illegally sold. The analytics may be able to spot such activity by comparing the frequency the doctor uses the particular diagnosis with the average frequency of other doctors in the same area. If the analytics indicate an abnormality, the information can be provided to the medical insurance provider or another third party for further investigation.

Various embodiments may comprise receiving an enrollment request from the medical consumer for a medical fraud alert service. A portion of the enrollment process may comprise an authentication step to verify that the medical consumer is the rightful owner of the medical identity. As part of this authentication step, the medical consumer may provide personal identifying information and identifying information for a medical insurance account. The identity of the medical consumer may be authenticated by providing to the medical consumer details for a several medical goods or services. A portion of the medical goods or services may be actual goods or services provided to the medical consumer and a portion may be fictitious medical goods or services. For example, FIG. 5 illustrates various embodiments of a screen shot 500 of an input screen that may display details 505 of several medical goods or services. The medical consumer may indicate which of the medical goods or services are accurate and which are inaccurate by clicking on the appropriate check box 510. Once the accuracy of each medical goods or services is indicated, the medical consumer may submit the responses by clicking the "enter" button 515. If the responses are correct, then the enrollment process may continue.

Figure 6:
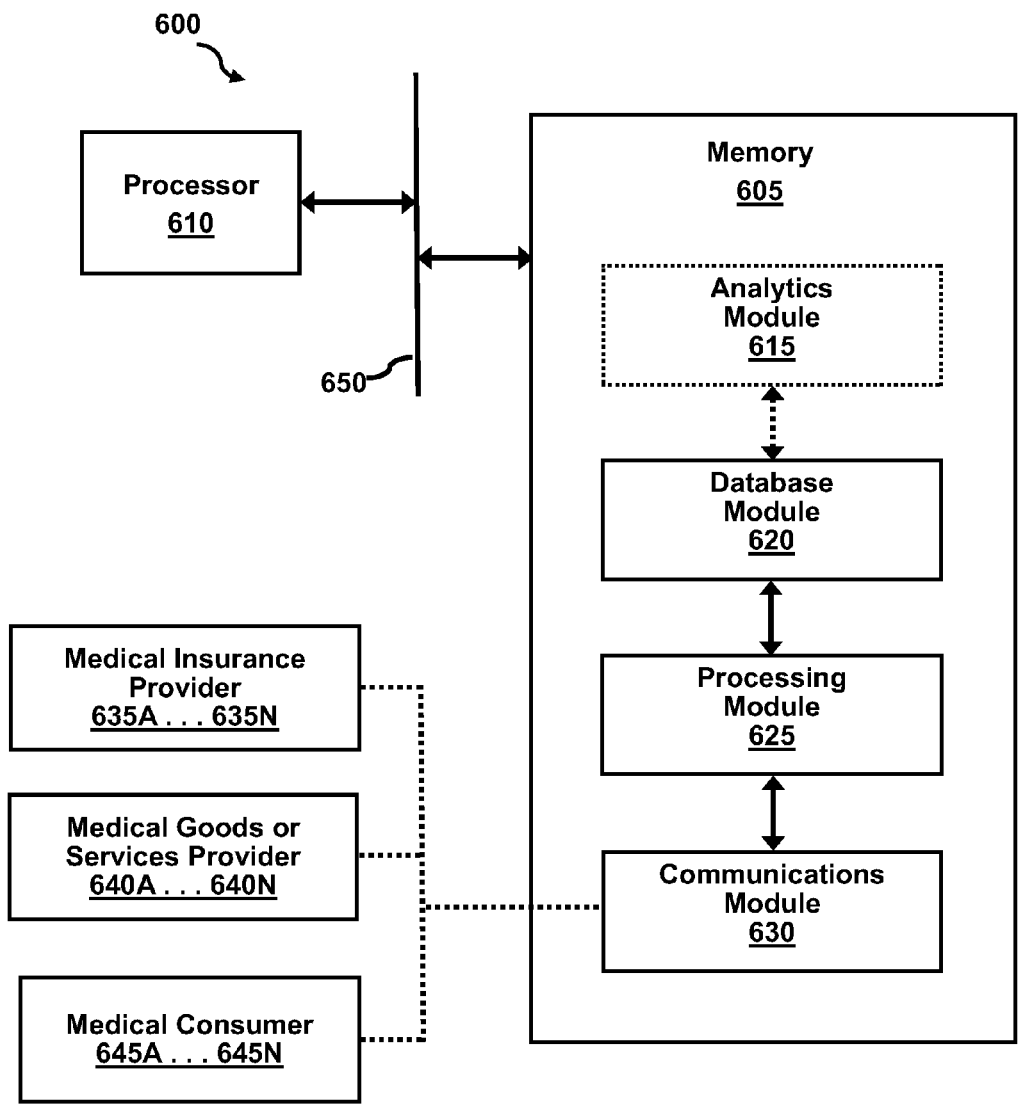
FIG. 6 is a schematic diagram of an exemplary architecture of a system for reducing fraudulent use of a medical identity to obtain medical goods or services according to various embodiments.

FIG. 6 illustrates a system 600 for reducing fraudulent use of a medical identity to obtain medical goods or services. System 600 may be comprised of a memory 605 for storing executable instructions and a processor 610 for executing the instructions stored in memory 605. The processor 610 and memory 605 may be connected by a single bus 650, or by any other connection device known in the art.

The executable instructions may be comprised of a plurality of modules. In various embodiments, the modules may include a database module 620 configured to receive new and updated information, store and organize the information, and retrieve the information. The information stored in the database module 620 may comprise medical claims data, medical insurance account identification information, medical consumer identification information, and medical goods or service provider information. The database module 620 may comprise a relational database such that relationships between the data, such as which medical claims data are associated with each provider of medical goods or services, as well as which medical consumers received the medical goods or services associated with each medical claim, are maintained.

A processing module 625 may also be present within the executable instructions that is communicatively coupled to the database module 620. The processing module 625 may execute requests from a variety of users to enter data, retrieve data, analyze data, add or delete users, and handle other operational requests within the system 600.

In addition, the executable instructions may further comprise a communications module 630 communicatively coupled to the processing module 625. The communications module 630 may also be communicatively coupled to a plurality of users, such as medical insurance providers 635A-635N, medical goods or service providers 640A-640N, and medical consumers 645A-645N (where N represents any number of the specific users). The communications module 630 may receive data from and transmit data to the users 635, 640, 645.

The executable instructions may optionally include analytics module 615 communicatively coupled to the processing module 625. The analytics module 615 may contain one or more algorithms for performing a variety of analyses on the medical claims data, or any other data stored by the database module 620.

According to some embodiments, the system 600 may include a cloud-based computing environment that collects, processes, analyzes, and publishes datasets. In general, a cloud-based computing environment is a resource that typically combines the computational power of a large grouping of processors and/or that combines the storage capacity of a large group of computer memories or storage devices. For example, systems that provide a cloud resource may be utilized exclusively by their owners, such as Google™ or Yahoo!™, or such systems may be accessible to outside users who deploy applications within the computing infrastructure to obtain the benefits of large computational or storage resources.

The cloud may be formed, for example, by a network of web servers with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depend upon the type of business associated with each user.

Figure 7:
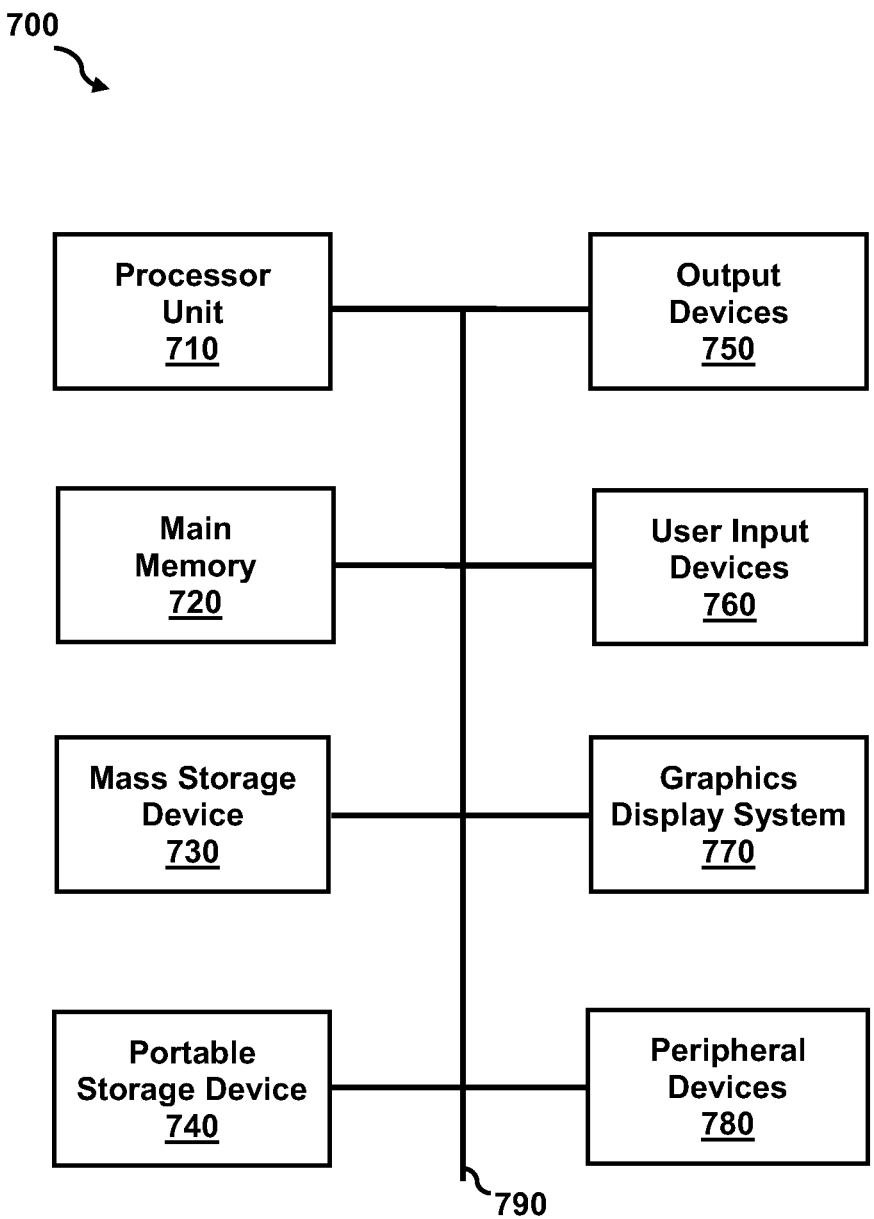
FIG. 7 is a block diagram of an exemplary computing system that may be utilized to practice aspects of the present disclosure according to various embodiments.

FIG. 7 illustrates an exemplary computing system 700 that may be used to implement an embodiment of the present technology. The computing system 700 of FIG. 7 includes one or more processor units 710 and main memory 720. Main memory 720 stores, in part, instructions and data for execution by processor 410. Main memory 720 can store the executable code when the system 700 is in operation. The system 700 of FIG. 7 may further include a mass storage device 730, portable storage device(s) 740, output devices 750, user input devices 760, a graphics display system 770, and other peripheral devices 780.

The components shown in FIG. 7 are depicted as being connected via a single bus 790. The components may be connected through one or more data transport means. Processor unit 710 and main memory 720 may be connected via a local microprocessor bus, and the mass storage device 730, peripheral device(s) 780, portable storage device(s) 740, and graphics display system 770 may be connected via one or more input/output (I/O) buses.

Mass storage device 730, which may be implemented with a magnetic disk drive or an optical disk drive, is a non-volatile storage device for storing data and instructions for use by processor unit 710. Mass storage device 730 can store the system software for implementing embodiments of the present technology for purposes of loading that software into main memory 720.

Portable storage device 740 operates in conjunction with a portable non-volatile storage media, such as a floppy disk, compact disk or digital video disc, to input and output data and code to and from the computer system 700 of FIG. 7. The system software for implementing embodiments of the present technology may be stored on such a portable media and input to the computer system 700 via the portable storage device 740.

User input devices 760 provide a portion of a user interface. User input devices 760 may include an alphanumeric keypad, such as a keyboard, for inputting alphanumeric and other information, or a pointing device, such as a mouse, a trackball, stylus, or cursor direction keys. Additionally, the system 700 as shown in FIG. 7 includes output devices 750. Suitable output devices include speakers, printers, network interfaces, and monitors.

Graphics display system 770 may include a liquid crystal display (LCD) or other suitable display device. Graphics display system 770 receives textual and graphical information, and processes the information for output to the display device.

Peripheral devices 780 may include any type of computer support device to add additional functionality to the computer system. Peripheral device(s) 780 may include a modem or a router.

The components contained in the computer system 700 of FIG. 7 are those typically found in computer systems that may be suitable for use with embodiments of the present technology and are intended to represent a broad category of such computer components that are well known in the art. Thus, the computer system 700 of FIG. 7 can be a personal computer, hand held computing system, telephone, mobile computing system, workstation, server, minicomputer, mainframe computer, or any other computing system. The computer may also include different bus configurations, networked platforms, multi-processor platforms, etc. Various operating systems can be used including UNIX, Linux, Windows, Macintosh OS, Palm OS, and other suitable operating systems.

Some of the above-described functions may be composed of instructions that are stored on storage media (e.g., computer-readable media). The instructions may be retrieved and executed by the processor. Some examples of storage media are memory devices, tapes, disks, and the like. The instructions are operational when executed by the processor to direct the processor to operate in accord with the technology. Those skilled in the art are familiar with instructions, processor(s), and storage media.

It is noteworthy that any hardware platform suitable for performing the processing described herein is suitable for use with the technology. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical or magnetic disks, such as a fixed disk. Volatile media include dynamic memory, such as system RAM. Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic media, a CD-ROM disk, digital video disk (DVD), any other optical media, any other physical media with patterns of marks or holes, a RAM, a PROM, an EPROM, an EEPROM, a FLASHEPROM, any other memory chip or data exchange adapter, a carrier wave, or any other media from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

The above description is illustrative and not restrictive. Many variations of the technology will become apparent to those of skill in the art upon review of this disclosure. The scope of the technology should, therefore, be determined not with reference to the above description, but instead should be determined with reference to the appended claims along with their full scope of equivalents.

What is claimed is:

1. A method comprising:

receiving an enrollment request from a hand-held personal digital assistant operated by a medical consumer for a medical fraud alert service;

in response to receiving the enrollment request, authenticating an identity of the medical consumer by providing to the hand-held personal digital assistant operated by the medical consumer details for a plurality of medical goods or services, wherein a portion of the plurality of medical goods or services are actual goods or services provided to the medical consumer and a portion are fictitious medical goods or services;

in response to the providing to the hand-held personal digital assistant operated by the medical consumer details for the plurality of medical goods or services, receiving a response from the hand-held personal digital assistant operated by the medical consumer indicating which of the plurality of medical goods or services are actual goods or services and which are fictitious goods or services;

receiving by a cloud-based fraud prevention server from a provider of medical insurance, medical billing, diagnostic or procedural codes associated with a medical insurance account of the medical consumer, the medical billing, diagnostic or procedural codes further comprising medical goods or medical services previously provided to the medical consumer by a provider of the medical goods or the medical services and submitted to the provider of medical insurance by the provider of the medical goods or the medical services;

analyzing by the cloud-based fraud prevention server the medical billing, diagnostic or procedural codes by comparing a frequency the provider cites a particular diagnosis against an average frequency of other providers citing the particular diagnosis;
determining if the frequency the provider cites the particular diagnosis meets or exceeds a predefined threshold for the average frequency of the other providers citing the particular diagnosis;
if the frequency exceeds the predefined threshold for the average frequency of the other providers citing the particular diagnosis, notifying the provider of medical insurance about potential fraud;
analyzing by the cloud-based fraud prevention server the medical billing, diagnostic or procedural codes by determining if the medical insurance account has been used to obtain a prescription from multiple providers of medical goods or medical services;
if the medical insurance account has been used to obtain the prescription from the multiple providers of medical goods or medical services, notifying the provider of medical insurance about potential fraud;
automatically securely transmitting by the cloud-based fraud prevention server the medical billing, diagnostic or procedural codes in the form of a text message to the hand-held personal digital assistant operated by the medical consumer; and
receiving by the cloud-based fraud prevention server a confirmation status from the hand-held personal digital assistant operated by the medical consumer for the medical billing, diagnostic or procedural codes; determining if the confirmation status indicates potential fraud; and if the confirmation status indicates potential fraud, notifying the provider of medical insurance.

2. The method of claim 1, wherein the medical insurance account comprises one or more of a name and address of the medical consumer, a name of an insurance provider, a policy number, a group number, and a member number.

3. The method of claim 1, wherein the medical billing, diagnostic or procedural codes comprise one or more of a name and address of a provider of the medical goods or services, a location where the medical goods or services were provided, a description of the medical goods or services, and a date that the medical goods or services were provided.

4. The method of claim 1, wherein transmitting the medical billing, diagnostic or procedural codes to the medical consumer comprises alerting the medical consumer that medical claims data have been received.

5. The method of claim 1, further comprising transmitting the medical billing, diagnostic or procedural codes to the medical consumer by sending an electronic mail message, a text message, a message delivered via a social media website, a telephone call, or a letter to the medical consumer.

6. The method of claim 1, wherein receiving confirmation status from the medical consumer comprises receiving one of:
confirmation from the medical consumer that the medical billing, diagnostic or procedural codes are accurate;
confirmation from the medical consumer that the medical billing, diagnostic or procedural codes are inaccurate; or
notification that the medical consumer is unable to determine the accuracy of the medical billing, diagnostic or procedural codes.

7. The method of claim 6, further comprising initiating further communications with the medical consumer when the medical consumer confirms that the medical billing, diagnostic or procedural codes are inaccurate or is unable to determine the accuracy of the medical billing, diagnostic or procedural codes.

8. The method of claim 6, further comprising notifying a provider of the medical insurance account when the medical consumer confirms that the medical billing, diagnostic or procedural codes are inaccurate or is unable to determine the accuracy of the medical billing, diagnostic or procedural codes.

9. The method of claim 1, wherein receiving confirmation status from the medical consumer comprises receiving notification that the medical consumer has viewed the medical billing, diagnostic or procedural codes.

10. The method of claim 1, wherein receiving confirmation status from the medical consumer comprises receiving an access request from the medical consumer to access a website containing the medical billing, diagnostic or procedural codes.

11. The method of claim 1, further comprising notifying a provider of the medical insurance account after a determination has been made that the medical billing, diagnostic or procedural codes may be fraudulent.

12. The method of claim 1, further comprising transmitting the confirmation status to a provider of the medical insurance account.

13. The method of claim 1, wherein medical goods or services comprises direct interaction with doctors, dentists, psychologists, therapists, chiropractors, nurses, assistants, hygienists, technicians, trainers, nutritionists, emergency medical technicians, social workers, and like health practitioners and professionals; prescription medications; laboratory services; high technology diagnostic services, tests, and procedures; transportation by ambulance; blood and blood products; durable medical equipment and associated supplies; eyeglasses and corrective lenses; external prosthetic, orthotic and corrective devices; internal medical devices; and the like.

14. The method of claim 1, further comprising transmitting a reminder to the medical consumer when the medical consumer fails to confirm the confirmation status of the medical billing, diagnostic or procedural codes after a predetermined period of time.

15. The method of claim 1, further comprising:
notifying the medical consumer of abnormal activity on the medical insurance account associated with the medical consumer;
requesting confirmation of the medical billing, diagnostic or procedural codes from the medical consumer; and
receiving a response to the confirmation request from the medical consumer.

16. The method of claim 1, wherein the confirmation status comprises one of:
the medical billing, diagnostic or procedural codes are accurate;
the medical billing, diagnostic or procedural codes are inaccurate; or
the accuracy of the medical billing, diagnostic or procedural codes cannot be readily determined.

17. The method of claim 1, further comprising determining the medical billing, diagnostic or procedural codes meet or exceed a predefined threshold for having a high probability of being legitimate and not securely transmitting the text message in order to increase responsiveness of the medical consumer to a future text message for medical billing, diagnostic or procedural codes not meeting or exceeding the predefined threshold and therefore having a lower probability of being legitimate and thereby improving functioning of the cloud-based fraud prevention server by reducing processor and memory resources required for securely transmitting text messages.

\* \* \* \* \*